United States Patent [19]
Amer

[11] Patent Number: 5,266,571
[45] Date of Patent: Nov. 30, 1993

[54] TREATMENT OF HEMORRHOIDS WITH 5-HT$_2$ ANTAGONISTS

[76] Inventor: Moh. Samir Amer, 3177 Padaro La., Carpinteria, Calif. 93013

[21] Appl. No.: 818,389

[22] Filed: Jan. 9, 1992

[51] Int. Cl.$^5$ .................... A61K 31/50; A61K 31/495
[52] U.S. Cl. .................................. 514/252; 514/253; 514/329; 514/882
[58] Field of Search ................ 514/252, 253, 324, 882

[56] References Cited

U.S. PATENT DOCUMENTS 4,539,318  9/1985  Baldwin et al. ...................... 514/222
4,665,075  5/1987  Vandenbeck et al. .............. 514/259

FOREIGN PATENT DOCUMENTS 0037265 10/1981 European Pat. Off. .
854161 6/1985 South Africa .

OTHER PUBLICATIONS

Frazer, Maavani & Wolfe; "Subtypes of Receptors for Serotonin" Annual Reviews of Pharmacology and Toxicology, vol. 30, 307–348 (1990).
Chemical Abstracts (Baldwin et al) 105:190476s 1986.

Primary Examiner—Leonard Schenkman
Attorney, Agent, or Firm—Samson B. Leavitt; Michael A. Leavitt

[57] ABSTRACT

This invention relates to a method for treating or preventing hemorrhoids, comprising administering to a susceptible animal a 5-hydroxytryptamine$_2$ (5-HT$_2$) receptor antagonist at an anti-hemorrhoidally effective therapeutic dose.

7 Claims, No Drawings

TREATMENT OF HEMORRHOIDS WITH 5-HT$_2$ ANTAGONISTS

FIELD OF THE INVENTION

This invention relates to a method and a class of pharmaceutical agents for treating hemorrhoids. The method comprises administering to a susceptible animal a 5-hydroxytryptamine-2 receptor antagonist (5-HT$_2$) at an anti-hemorrhoidally effective therapeutic dose.

BACKGROUND OF THE INVENTION

Serotonin or 5-hydroxytryptamine or 5-HT is a vasoconstrictor and a powerful stimulant of a variety of smooth muscles and nerves. A derivative of the amino acid tryptophan, 5-HT is formed predominantly in enterochromaffin or argentaffin cells of the intestinal tract. It is transported in the blood by platelets and is present in the brain and other tissues. Its pharmacological actions result in a variety of responses involving, inter alia, the cardiovascular, respiratory, and gastrointestinal systems, smooth muscles, exocrine glands, carbohydrate metabolism, sensory nerve endings, autonomic ganglia, the adrenal medulla, and the central nervous system.

Receptors are molecules embedded in outer cell membranes, the main function of which are to recognize and interact with hormones that come in contact with the cell. They act as locks, while the hormones act as keys. Each key (hormone) fits the lock (receptor) that interacts with it and with it alone. Once the key (hormone) fits the lock (receptor), the reaction to the hormone is triggered within the cell. Cellular reaction is therefore determined by the type and number of receptors on the outer membrane of the cells. Consequently, one hormone can trigger different responses in different cells because it may have different receptors. Thus, the same hormone that can contract one smooth muscle cell, can also relax a skeletal muscle cell having a different receptor to the same hormone. This is true for 5-HT.

There are many receptors for 5-HT that control the various cellular responses which are mentioned above. To identify the different receptors to a specific hormone (e.g. 5-HT), several methods are used. For example, in labeling studies, the labeled hormone binds to a specific receptor. The antagonists are classified according to their ability to displace the labeled hormone from the receptor in question. Those that can displace it from a particular receptor are said to be antagonists to that receptor. Some antagonists can displace the hormone from one receptor without affecting its binding to another, and the degree of selectivity can thus be determined. In pharmacological studies, the ability of antagonists to antagonize some of the effects of the hormone thought to be related to one receptor or another are examined. A suitable example relates to the hormone histamine. Some antagonists (histamine-2 antagonists) can antagonize its acid secretory receptors with little or no effect on its lung receptors and thus inhibit acid secretion by the stomach without causing bronchodilatation. Other antagonists (histamine-1 antagonists) antagonize histamine's lung effects with almost no activity against its acid secretory effects. Biochemical studies are those in which the biochemical effects of the hormone in question can be antagonized selectively by one receptor antagonist or another.

Serotonin receptors are divided into several classes, one of which is referred to as the 5-HT$_2$ receptor. A complete discussion of such receptors will be found in "The Peripheral Actions of 5-Hydroxytryptamine" edited by John R. Fozard (Oxford University Press, 1989). Based on a combination of the above studies, the 5-HT$_2$ receptor has been identified, although some subclasses of it also seem to exist. Its binding to 5-HT is antagonized by specific 5-HT$_2$ antagonists such as ketanserine and mesulergine. It acts by modulating phosphatidylinositol turnover, but this effect is inhibited by mianserin and ketanserin. It is present in the brain cortex, blood platelets and vascular smooth muscles. Stimulation of this receptor causes a detectable inward current due to elevated intracellular calcium ion levels in nervous tissue. It causes aggregation of the blood platelets and contraction of the vascular smooth muscles.

Hemorrhoids are a varicose dilatation of veins in the superior or inferior hemorrhoidal plexus. More commonly, hemorrhoids refer to a mass of dilated veins in swollen tissue situated near the anal sphincter. They are believed to result from a persistent increase in venous pressure, which may be due, in part, to a constriction of the large downstream colonic veins. Occlusion due to platelet aggregation and thrombus formation may also contribute to the symptoms of hemorrhoids by interrupting blood flow and increasing blood stasis and tissue congestion.

5-HT$_2$ antagonist compounds have traditionally been used as anti-anxiety agents, antidepressants, antipsychotics, antimigraine agents or as modifiers of certain other CNS functions.

OBJECTS OF THE INVENTION

It is an object of this invention to provide a novel method to treat or prevent hemorrhoids.

It is another object of this invention to use in such method a class of compounds hitherto employed for other purposes.

Other objects and advantages will appear as the description proceeds.

SUMMARY OF THE INVENTION

The attainment of one or more of such objects is made possible by this invention, which, according to certain of its aspects, includes a method comprising administering to a susceptible animal, including a human, a 5-HT$_2$ receptor antagonist at an anti-hemorrhoidally effective therapeutic dose, which does not cause undesirable side effects. Preferred 5-HT$_2$ antagonists include 2'[2-(1-methyl-2-piperidyl)ethyl] cinnamanilide hydrochloride; 2-[3-[4-(3-chlorophenyl)-1-piperazinyl]-propyl-5-ethyl-2,4-dihydro-4-(2-phenoxyethyl)-3H-1,2,4-triazol-3-one hydrochloride; 8-[4-[4-(1,2-benzisotriazol-3-yl)-1-piperazinyl]butyl]-8-azaspiro[4,5]decane-7,9-dione hydrochloride and any mixture thereof.

This invention is based upon the discovery that 5-HT plays an important role in mediating both the increase in venous pressure and/or platelet clumping that lead to the congestion of the veins in the hemorrhoidal plexus and that 5-HT$_2$ receptors rather than 5-HT$_1$ receptors are involved, and that 5-HT$_2$ antagonists are useful in the treatment of hemorrhoids.

These compounds may be administered in admixture with a pharmaceutically acceptable carrier.

In in vitro lab tests, agents of this invention were shown to block the contractile effect of 5-HT on the human colon.

DETAILED DESCRIPTION OF THE INVENTION

This invention relates to a new use for a known class of pharmaceutical agents, which may be administered to an animal, including mammals in general and humans in particular, which are prone to hemorrhoids. These agents comprise the 5-HT$_2$ receptor antagonists, and the analogs and derivatives thereof which exhibit anti-hemorrhoidal activity, and they are administered at an anti-hemorrhoidally effective dose that does not cause adverse side effects. These pharmacological agents may be administered in admixture with a pharmaceutically acceptable carrier.

In a series of experiments using rings of human colon veins, representative 5-HT$_2$ receptor antagonists were found to produce highly surprising results in blocking the contractile effects of 5-HT on the human colon. Human colonic vein rings were isolated from discarded human colon tissue following surgery (colostomy). The rings were prepared immediately after surgery and were suspended in buffered physiological saline. The contractions produced by the rings in response to the addition of 5-HT in vitro were measured. The effects of three selected 5-HT$_2$ antagonist compounds on antagonizing 5-HT contractile effects were also determined.

The following tables list the three compounds used and the activity of each in blocking the contractile effects of 5-HT on the human colon in vitro. Table A also includes the activities of the three compounds on four other receptors to determine receptor selectivity.

Compound I as used herein has the chemical formula: 2'[2-(1-methyl-2-piperidyl)ethyl] cinnamanilide hydrochloride, and has the following structural formula:

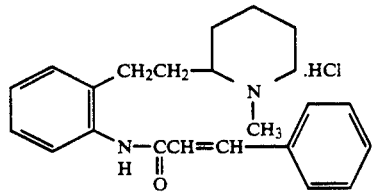

Compound II as used herein has the chemical formula: 2-[3-[4-(3-chlorophenyl)-1-piperazinyl]propyl-5-ethyl-2,4-dihydro-4-(2-phenoxyethyl)-3H-1,2,4-triazol-3-one hydrochloride, and has the following structural formula:

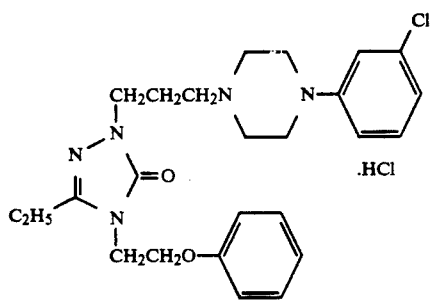

Compound III as used herein has the chemical formula: 8-[4-[4-(1,2-benzisotriazol-3-yl)-1-piperazinyl]butyl]-8-azaspiro[4,5]decane-7,9-dione hydrochloride, and has the following structural formula:

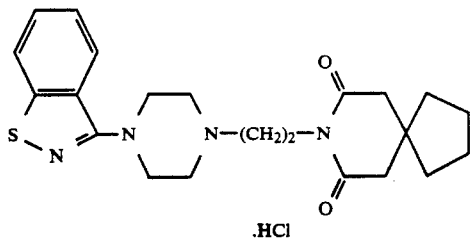

TABLE A

| Receptor | Receptor Blocking Profile (IC-50; nm) [nM==nanomolar or 1 × 10$^{-9}$M] | | |
|---|---|---|---|
| | Compound I | Compound II | Compound III |
| 5-HT$_2$ | 3.4 | 17.0 | 1.7 |
| 5-HT$_1$ | 22,000.0 | >1,000.0 | 12.5 |
| Dopamine-2 | >1000.0 | >1000.0 | 8.4 |
| Alpha-receptor | >1000.0 | 160.0 | 47.0 |

The IC-50 is the concentration that inhibits agonist binding to the receptor by 50%. The better the blocker a compound is, the smaller is the concentration thereof needed to block the receptor, i.e., the smaller the IC-50, the better receptor blocker or antagonist the compound is.

The receptor blocking profile is determined as follows: Labeled 5-HT is mixed with a purified preparation containing the receptor. The amount of labeled material that attaches itself to the receptor and cannot be washed off is calculated. In a series of other similar tubes, the same quantity of labeled 5-HT is mixed with increasing concentrations of the antagonist which will antagonize the binding of 5-HT to the receptor. Decreasing quantities of the labeled material will bind to the receptor. The concentration of the antagonist that inhibits the binding by 50% is then calculated.

TABLE B

| Activity against 5-HT on the human colon in vitro | | | |
|---|---|---|---|
| IC-50 | 2 ×10$^{-9}$ (I) | 10$^{-8}$ (II) | 10$^{-9}$ (III) |

This activity is determined as follows: Rings of human colon veins are prepared and hung in a tissue bath. The contractions of the rings are monitored. Adding 5-HT causes the rings to contract. Pre-addition of increasing concentrations of the antagonist result in lesser contractions. The amount of antagonist causing a 50% inhibition of the contractions is then calculated.

As is evident from the above data, although the compounds I, II, and III possess widely different activities against the different receptors tested, their activities in blocking the contractile effects of 5-HT on human colon rings correlated best with their 5-HT$_2$ blocking potencies.

Since these three compounds differ significantly from each other chemically, the conclusion is inescapable that their antagonism of the effects of 5-HT on the human colon is due primarily to their function in blockading the 5-HT$_2$ receptors in that tissue. Thus, other 5-HT$_2$ antagonists, irrespective of their chemical structure or other properties, should antagonize 5-HT and block its contractile effects on the human colon. This activity represents the basis of the value of this class of pharmacological agents in the prevention or treatment of hemorrhoids in man and other animals.

5-HT$_2$ antagonists, in addition to blocking the effects of 5-HT, also possess other useful pharmacological effects that may enhance their value in the treatment of hemorrhoids. These other effects include their well documented analgesic activities, their local anesthetic properties, their ability to inhibit spontaneous smooth muscle spasms (e.g., in the uterus) and platelet aggregation, and their antagonism of the edema induced by 5-HT.

The 5-HT$_2$ antagonists of this invention may be used topically or systemically, and they may be taken orally, in liquid, powder, tablet or capsule form; parenterally, by intravenous, subcutaneous, or intramuscular injection; topically by direct application to the colon in the form of a cream, gel, or ointment; rectally by suppository or enema; or by inhalation therapy.

Suitably the compositions of this invention consist of sufficient material to provide a dose of from 0.05–10 mg. per kg. of body weight, more suitably 0.2–6 mg/kg body weight. These compositions may be taken 1–3 times daily or as needed until the hemorrhoids or the pain or symptoms thereof have subsided.

The 5-HT$_2$ receptor antagonists of this invention may be prepared and used in any suitable solid or liquid form, e.g. powder, paste, tablet, lozenge, gel, chewing gum, solution, suspension, emulsion, aerosol or the like. These compositions may contain the active ingredient in amounts ranging from less than 1% to over 99%, with the remainder being a pharmaceutically acceptable solid or liquid carrier, which may contain other conventional excipients. Examples of such carriers and excipients include fillers, binders, flavors, sweeteners, bulking and coloring agents, antioxidants, anionic, nonionic, cationic, zwitterionic, and amphoteric surface active detergents, sudsing, dispersing and emulsifying agents, buffering and pH adjusting agents, water and organic solvents, humectants, thickeners, preservatives, stabilizers, mold release agents, disintegrants, anti-disintegrants, lubricants and the like. Examples of conventional pharmaceutically acceptable carriers and excipients are profusely disclosed in the prior art including discussions in U.S. Pat. No. 4,515,772 (Parran et al, Proctor & Gamble), U.S. Pat. No. 4,966,777 (Gaffar et al, Colgate-Palmolive Company), and U.S. Pat. No. 4,728,512 (Mehta et al, American Home Products), which discussions are incorporated herein by reference thereto.

Generally speaking, this invention is directed to a method for treating or preventing hemorrhoids in an animal or human body. The method comprises administering to such an animal or mammal, especially humans, an anti-hemorrhoidally effective amount of an 5-HT$_2$ receptor antagonist. It will be understood that the foregoing discussion only illustrates the invention and its principles. However, many modifications and variations in the details of the disclosure will occur to those skilled in the art to which this invention relates and still remain within the scope and principles of the invention. For example, the illustrative embodiments of the invention deal primarily with several specific 5-HT$_2$ receptor antagonists. It is apparent, however, that the principles of the invention can be applied to other 5-HT$_2$ receptor antagonists as well.

This invention has been disclosed with respect to preferred embodiments, and it will be understood that variations and modifications thereof obvious to those skilled in the art are intended to be included within the spirit and purview of this application and the scope of the appended claims.

What is claimed is:

1. A method for treating or preventing hemorrhoids, which comprises administering to a hemorrhoidally afflicted or susceptible animal a 5-HT$_2$ receptor antagonist at an anti-hemorrhoidally effective therapeutic dose.

2. The method of claim 1 wherein said 5-HT$_2$ receptor antagonist is a compound selected from the group consisting of 2'[2-(1-methyl-2-piperidyl)ethyl] cinnamanilide hydrochloride; 2-[3-[4-(3-chlorophenyl)-1-piperazinyl]propyl-5-ethyl-2,4-dihydro-4-(2-phenoxyethyl)-3H-1,2,4-triazol-3-one hydrochloride; 8-[4-[4-(1,2-benzisotriazol-3-yl)-1-piperazinyl]butyl]-8-azaspiro[4,5]decane-7,9-dione hydrochloride, analogs and derivatives thereof which function as anti-hemorrhoidally active 5-HT$_2$ antagonists, and any mixtures thereof.

3. The method of claim 1 wherein said 5-HT$_2$ receptor antagonist is administered by a method selected from the group consisting of intravenous injection, intramuscular injection, subcutaneous injection, oral administration, topical administration, rectal administration, or by inhalation therapy.

4. The method of claim 3 wherein said 5-HT$_2$ receptor antagonist is administered in admixture with a pharmaceutically acceptable carrier.

5. The method of claim 2 wherein said 5-HT$_2$ receptor antagonist is administered topically or systemically.

6. The method of claim 1 wherein said animal is a human.

7. The method of claim 2 wherein said animal is a human.

* * * * *